(12) United States Patent
Gamard

(10) Patent No.: US 12,107,811 B2
(45) Date of Patent: Oct. 1, 2024

(54) METHOD FOR ARCHIVING A PARTICULAR EVENT IN A LIFE OF A WEARER OF A CONNECTED WATCH

(71) Applicant: SWATCH AG, Biel/Bienne (CH)

(72) Inventor: Stéphane Gamard, Neuchâtel (CH)

(73) Assignee: SWATCH AG, Biel/Bienne (CH)

( * ) Notice: Subject to any disclaimer, the term of this patent is extended or adjusted under 35 U.S.C. 154(b) by 0 days.

(21) Appl. No.: 18/056,523

(22) Filed: Nov. 17, 2022

(65) Prior Publication Data

US 2023/0198925 A1 Jun. 22, 2023

(30) Foreign Application Priority Data

Dec. 21, 2021 (EP) .................................. 21216578

(51) Int. Cl.
*H04L 51/21* (2022.01)

(52) U.S. Cl.
CPC .................................... *H04L 51/21* (2022.05)

(58) Field of Classification Search
CPC ....... A61B 5/681; H04L 51/21; G04G 21/025
See application file for complete search history.

(56) References Cited

U.S. PATENT DOCUMENTS

| | | | |
|---|---|---|---|
| 11,051,704 B1 | 7/2021 | Tran | |
| 2016/0066829 A1* | 3/2016 | Sales | A61B 5/369 600/595 |
| 2016/0344918 A1* | 11/2016 | Tao | H04N 23/63 |
| 2017/0011210 A1 | 1/2017 | Cheong et al. | |
| 2017/0020444 A1* | 1/2017 | Lurie | A61B 5/74 |
| 2017/0169826 A1* | 6/2017 | Örthagen | H04R 29/004 |
| 2017/0324861 A1 | 11/2017 | Ferdman et al. | |
| 2018/0220973 A1* | 8/2018 | Asianto | A61B 5/681 |
| 2018/0234622 A1* | 8/2018 | Bostick | H04N 23/64 |
| 2018/0335756 A1* | 11/2018 | Kim | G04B 45/0015 |
| 2018/0365570 A1* | 12/2018 | Koukoumidis | G06F 40/30 |
| 2019/0371344 A1* | 12/2019 | Noh | G06V 40/174 |
| 2021/0311906 A1 | 10/2021 | Soon-Shiong | |
| 2022/0036554 A1* | 2/2022 | Greenwood | G06V 40/20 |
| 2022/0304603 A1* | 9/2022 | Freckleton | G16H 50/20 |

FOREIGN PATENT DOCUMENTS

| | | |
|---|---|---|
| JP | 2017-527007 A | 9/2017 |
| WO | 2016/010769 A2 | 1/2016 |
| WO | 2017/200806 A1 | 11/2017 |

OTHER PUBLICATIONS

European Search Report for EP 21216578 dated Apr. 19, 2022.

\* cited by examiner

*Primary Examiner* — Boris D Grijalva Lobos
(74) *Attorney, Agent, or Firm* — Sughrue Mion, PLLC

(57) ABSTRACT

A method for archiving a particular event in a life of a wearer of a connected watch. The method includes: tracking at least one category of emotional factor of the wearer, diffusing, by the connected watch to the wearer, a notification of detection of the particular event to the wearer based on a change in the tracked at least one category of emotional factor of the wearer occurring; designing, in response to the notification, a multimedia message relating to the particular event; and sending the multimedia message to a database of a server configured to archive messages, including the multimedia message, that relate to particular events of the wearer.

10 Claims, 2 Drawing Sheets

METHOD FOR ARCHIVING A PARTICULAR EVENT IN A LIFE OF A WEARER OF A CONNECTED WATCH

CROSS-REFERENCE TO RELATED APPLICATIONS

This application claims priority to European Patent Application No. 21216578.1 filed Dec. 21, 2021, the entire contents of which are incorporated herein by reference.

FIELD

Embodiments of the present disclosure relate to a method for archiving a particular event in a life of a wearer of a connected watch, and a system for archiving this particular event implementing such a method.

BACKGROUND

Everyone's life is strewn with many events. School, family, work, life learning, hobbies, travel, and history are life sequences in which each person often experiences significant events.

Furthermore, the memory of each of these significant events is unique for each person, since each person has a different perspective and experience of the events.

In this context, a general problem is related to the fact that it is often difficult to remember precisely some of these life events.

In the related art, it is known to use methods implemented by Internet sites which make it possible to archive images or videos relating to significant life events and which can be consulted at any time.

SUMMARY

Embodiments of the present disclosure provide an alternative to the existing methods.

To this end, embodiments of the present disclosure include a method for archiving a particular event in a life of a wearer of a connected watch comprising the following steps:
  tracking at least one category of emotional factor of the wearer;
  diffusing a notification of detection of the particular event by the connected watch to the wearer when a change in the tracked at least one category of emotional factor of the wearer has occurred;
  designing a multimedia message relating to the particular event in response to this notification, and
  storing the multimedia message in a database of server configured to archive such messages relating to particular events of the wearer.

In other embodiments:
  the method comprises a step of displaying on the interface for broadcasting a visual piece of information of the connected watch, a specific interface for entering the multimedia message relating to the particular event lived by the wearer, after the notification has been diffused;
  the designing the multimedia message comprises creating, by the connected watch, the multimedia message by using a specific interface displayed on the interface for broadcasting a visual piece of information of the connected watch;
  the step of designing the multimedia message comprises a sub-step of creating this message from the connected watch;
  the step of designing the multimedia message comprises a sub-step consisting in completing this multimedia message from an electronic device;
  the step of tracking includes a sub-step for detecting a change in measuring data of the emotional factor coming from a bio-information sensor included in the connected watch;
  the step of tracking includes a sub-step for detecting comprising a phase for monitoring the measuring data received in which each emotional factor measurement included in the measuring data, is compared to a reference measurement of this emotional factor;
  the step of tracking includes a sub-step for detecting comprising a phase of generating a detection message based on successive measurements of that emotional factor provided by the measuring data exceeding the reference measurement of this emotional factor during a predetermined period;
  the step of diffusing a notification comprises a sub-step of generating a notification based on a detection message.

Embodiments of the present disclosure also include a system for archiving a particular event in a life of a wearer of a connected watch performing this method, the system comprising the connected watch, which is equipped with a bio-information sensor; an electronic device; and a server including a database configured to archive multimedia messages relating to particular events of the wearer.

Embodiments of the present disclosure also include a system for archiving a particular event in a life of a wearer of a connected watch, implementing the method according to the preceding claims, the system comprising the connected watch and an electronic device configured for tracking at least one category of emotional factor of the wearer, in this system the connected watch is also configured for:
  diffusing to the wearer, a notification of detection of the particular event to the wearer based on a change in the tracked at least one category of emotional factor of the wearer occurring, and
  designing, in response to the notification, a multimedia message relating to the particular event; and
  the electronic device is also configured for sending the multimedia message to a database of a server of this system which is configured to archive messages, including the multimedia message, that relate to particular events of the wearer. In other embodiments:
  the electronic device is configured for completing the multimedia message during its designing;
  the connected watch is configured for displaying on the interface for broadcasting a visual piece of information of the connected watch, a specific interface for entering the multimedia message relating to the particular event lived by the wearer directly/immediately after this notification has been diffused;
  the connected watch is configured for displaying on the interface for broadcasting a visual piece of information of the connected watch, a specific interface for entering the multimedia message relating to the particular event lived by the wearer solely when the processing unit of the connected watch has detected that the wearer has received this notification;
  the connected watch is configured for designing a multimedia message by creating this message from a specific interface displayed on the interface for broadcasting a visual piece of information of the connected watch.

Embodiments of the present disclosure also include a non-transitory computer readable medium having stored thereon instructions for causing a connected watch, an electronic device, and a server to perform this method.

Embodiments of the present disclosure also include a computer program, optionally stored on a medium, comprising instructions for causing a connected watch, an electronic device, and a server to perform this method.

BRIEF DESCRIPTION OF THE DRAWINGS

Non-limiting example embodiments of the present disclosure will be described subsequently in more detail with reference to the attached drawing, in which.

DETAILED DESCRIPTION

Figure 1:
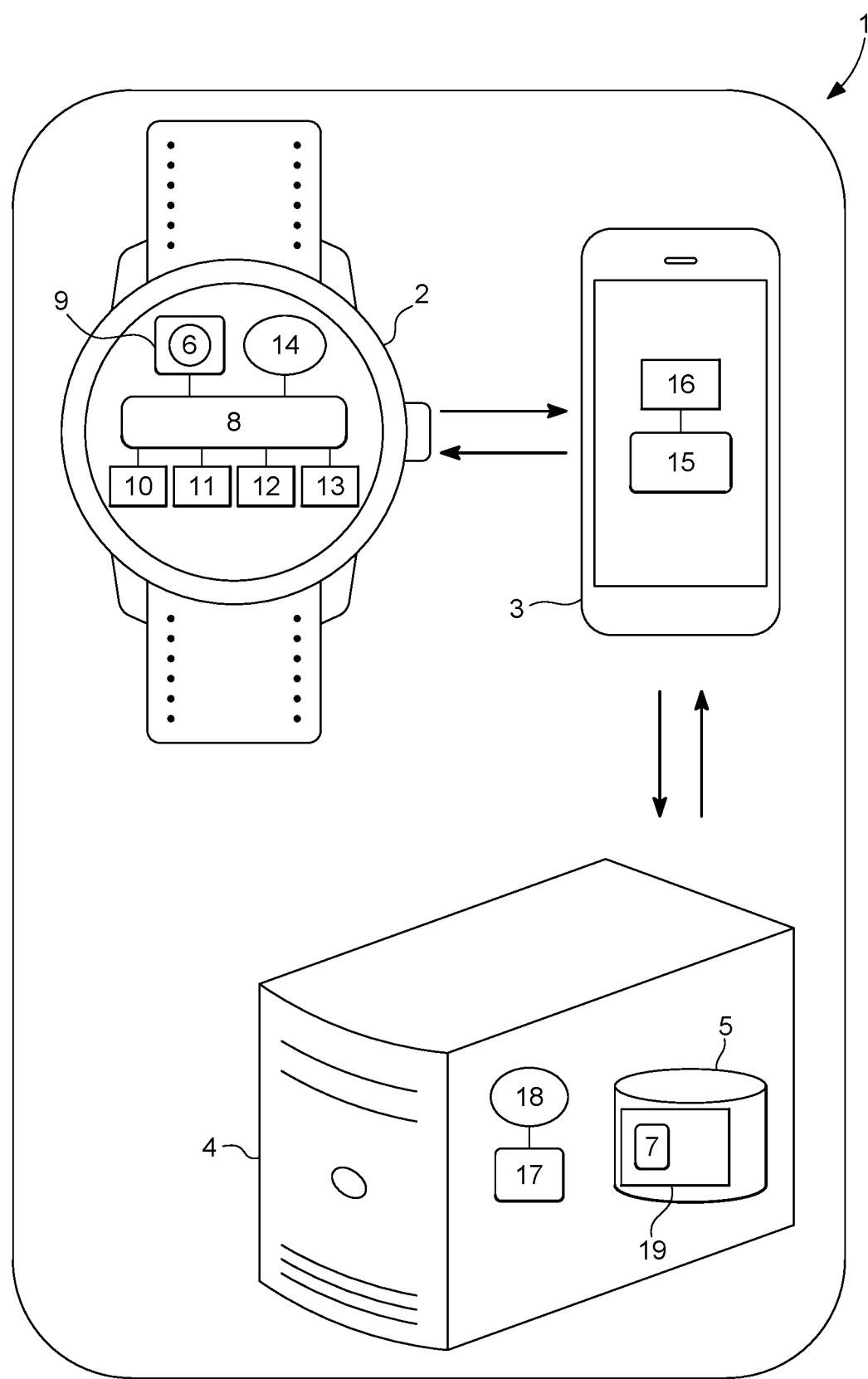
FIG. 1 is a schematic diagram illustrating a system for archiving a particular event in a life of a wearer of a connected watch according to embodiments of the present disclosure.

Referring now to the drawings, a system 1 and a method for archiving a particular event in the life of a wearer of a connected watch 2 of embodiments of the present disclosure, is explained in detail.

Briefly, this system 1 and method, allow the wearer to keep a memory of a particular event in his life, this particular event being identified from the detection of the emotional changes of this wearer. Moreover, this system 1 and method, allow the wearer to choose/select the particular event in his life for which he decides to record contrary to the systems and methods known in this technical field which automatically record, without distinction, all the events of the wearer's life which are detected. In other words, in the invention, the events detected are recorded with the consent of the wearer of the connected watch.

The particular event can be defined as being a fact, which has a significant impact in the life of this wearer. For instance, a young woman learning that she is pregnant is a good illustration of this particular event.

Referring firstly to FIG. 1, this system 1 comprises the connected watch 2, an electronic device 3, and a server 4 including a database 5. This system 1 also comprises a wireless or wired network architecture connecting the electronic device 3, the connected watch 2, and the server 4 together.

In this system 1, the connected watch 2 comprises a body such as a watch case, and an attachment element such as a wristlet allowing to fasten this body, for example to the wrist of the wearer. More specifically, this connected watch 2 comprises in a non-limiting and/or non-exhaustive manner:

processing unit 8 (also referred to as a "controller") including hardware and software resources, in particular at least one processor cooperating with memory elements;

an interface 9, for broadcasting a visual piece of information, such as a digital display;

an interface 10, for broadcasting an audio piece of information, such as a loudspeaker;

a wireless communication interface 11 (e.g., cellular, WLAN Bluetooth, etc.);

an input interface 12 such as a touch interface comprised, for example, in the interface for broadcasting a visual piece of information;

a microphone 13, and a bio-information sensor 14 measuring the bio-information of the wearer.

In this connected watch 2, the processing unit is connected, among others, to the interfaces 9, 10 for broadcasting a visual and sound piece of information, to the input interface 12, to the microphone 13, as well as to the wireless communication interface 11 and to the bio-information sensor 14. According to embodiments, the bio-information sensor 14 can be arranged in the caseback of the connected watch 2 and/or in the attachment element.

As previously specified, the bio-information sensor 14 measures the bio-information of the wearer. This bio-information is mainly related to various emotional factors connected with the behavioural and physiological characteristics of the wearer. In this context, the bio-information comprises several categories of emotional factor enumerated hereafter in a non-limiting and non-exhaustive way: breathing, amount of sweat, heartbeat, breathing, wink, eye-ball movement, gazing time, pupil diameter, blood pressure, brain wave, body movement, posture, skin temperature, galvanic skin response (GSR), micro-vibration (MV), electro-myography (EMG), and blood oxygen saturation (SPO2). These categories of emotional factor may be measured by cardiographic measurement units, EMG measurement units, head electrical voltage measurement units, infrared image intensity analyses, pressure sensors, temperature sensors, or sweating sensors. The bio-information sensor 14 may be configured to be supported by the wearer at a location such that it can detect this emotional factor, for example, the wearer's heartbeats or worn by the wearer at a location where it is in contact with the wearer's skin, and as such is able to measure parameters such as resistance.

In this system 1, the server 4 (such as a remote server) includes the database 5 capable of comprising a plurality of data relating to information about a plurality of wearer and for each of them at least one multimedia message 7 relating to particular events of the wearer.

This server 4 also comprises a control unit 17 (also referred to as a "controller") and a communication unit 18. In this server 4, the control unit 17 includes hardware and software resources, in particular at least one processor cooperating with memory components. This control unit 17 is capable of executing instructions for implementing a computer program configured to, for example, manage database 5 of server 4, and process the queries/instructions/data coming/sent to/from the electronic device 3, particularly to/from processing unit 15 thereof.

Furthermore, the electronic device 3 in this system 1 can comprise, for example: a computer, a smartphone or even a tablet. Such an electronic device 3 can be mobile and/or portable and/or compact. This electronic device 3 includes, in a non-limiting and/or non-exhaustive manner:

the processing unit 15 (also referred to as a "controller") including hardware and software resources, in particular at least one processor cooperating with memory elements;

a display module such as a screen displaying a visual representation of information data;

an interface, for audio information transmission, such as a loudspeaker;

a communication interface 16 allowing the electronic device 3 to establish a communication connection with the server 4 or with the connected watch 2;

a selection interface such as a keyboard or even a touch-sensitive interface;

at least one audio stream capture module comprising at least one microphone; and a module for acquiring at least one image, the module comprising at least one image sensor.

In this electronic device 3, the processing unit 15 is connected, inter alia, to the broadcast interface, to the communication interface 16, to the acquisition module and to the selection interface. The communication interface of this electronic device 3 comprises communication elements for receiving and transmitting data remotely via the cellular telephone network, a data network of the IP type via the telephone network or a data network of the IP type via a medium-range network, for example WI-FI or a short-range network implementing Bluetooth technology.

In addition, this electronic device 3, processing unit 15 is connected, among other things, to display module, to the transmission interface, to the communication interface and to selection interface. This processing unit 15 is capable in particular of executing instructions for implementing the computer program that is configured to process, for example, the queries/instructions/data being received/sent:

to/from server 4, particularly to/from control unit 17 thereof, and/or to/from the processing unit 8 of the connected watch 2.

Furthermore, the processing unit 15 of this electronic device 3 is able to execute a computer program also called an application or apps. More precisely in this context, the application is an "application of particular events". This application, when this processing unit 15 executes it, is able to participate in implementation of part of the steps of the method described below.

Figure 2:
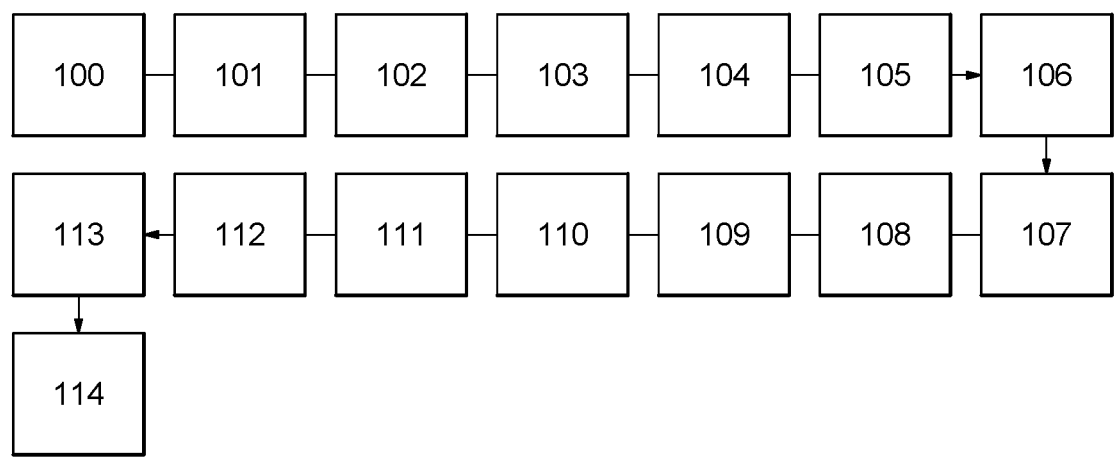
FIG. 2 is a flowchart relating to a method for archiving this particular event, according to embodiments of the present disclosure.

The system 1 is capable of implementing a method for archiving the particular event in the life of the wearer of the connected watch 2, shown in FIG. 2.

Such a method starts with a step of connecting 100 the connected watch 2 to the electronic device 3. During this step 100, the processing units 8, 15 of the connected watch 2 and the electronic device 3 connect to each other by means of their communication interface 11, 16 by using, for example, the Bluetooth™ protocol.

Once this connection is established, the application of particular events is active on the electronic device 3 and is able to exchange data with the processing unit 8 of the connected watch 2. In other words, the application is active as soon as the processing unit 15 of the electronic device 3 detects that the connection is established between the connected watch 2 and this electronic device 3.

Then, the method includes a step of tracking 101 at least one category of emotional factor of the wearer. It is understood that several categories can also be tracked simultaneously during the implementation of this step 101.

As understood from by below, this step 101 is implemented by the processing unit 15 of the electronic device 3 executing the application and also by the processing unit 8 of the connected watch 2 which is connected to the bio-information sensor 14.

In this context, this step of tracking 101 comprises a sub-step of receiving 102 measuring data of the emotional factor from the bio-information sensor 14. The measuring data may be specifically received by the processing unit 8 of the connected watch 2 and then sent, during a sub-step of transmitting 103, to the processing unit 15 of the electronic device 3 executing the application In this context, this application executed by the processing unit 15, is configured to participate in the detection of a particular event in the life of the wearer from the measurement data received. The step of tracking 101 includes to that end a sub-step for detecting 104 a change in the measuring data of the emotional factor. Such a sub-step 104 includes a phase for monitoring 105 the measuring data received. During this phase 105, each emotional factor measurement included in the measuring data, is compared to a reference measurement of this emotional factor. This reference measurement can be considered to be a threshold value. Moreover, this sub-step 104 comprises a phase of generating 106 a detection message if, during a predetermined period, successive measurements of that emotional factor provided by the measuring data exceed the reference measurement of this emotional factor. In this context, if the category of emotional factor is heartbeat, a detection message is generated based on the wearer's heart rate increasing by (or to) an amount that is greater than the reference measurement of this emotional factor within a given time period.

Furthermore, this sub-step 104 includes a phase of recording 107 information regarding the successive emotional factor measurements. In the context that the category of emotional factor is heartbeat, this information may relate to the wearer's heart rate at that time.

Then, the method comprises a step of diffusing 108 a notification 6 of the detection of the particular event by the connected watch 2 to the wearer when a change in the tracked at least one category of emotional factor of the wearer has occurred. Such a step 108 comprises a sub-step of receiving 109 the message of detection from the electronic device 3 and more specifically from the processing unit 15 executing the application. Then this step comprises a sub-step of generating 110 a notification 6 based on this message. For example, this notification 6 can be a vibration of the case watch of this connected watch 2 and/or a graphical representation notification 6 display on the digital display 9 of this watch 2 notably in full screen and/or a sound emitted by the loudspeaker 10 of this watch 2.

Then, the method includes a step of displaying on the interface 9, for broadcasting a visual piece of information of the connected watch, a specific interface, or a specific graphical interface, for entering a multimedia message 7 relating to the particular event lived by the wearer, after the notification has been diffused. During this step, the specific interface is displayed directly/immediately after this notification has been diffused. In an alternative, the specific interface is displayed when the processing unit of the connected watch has detected that the wearer has received this notification. This detection of this notification can be realised based on the interaction of the wearer with the connected watch in order to acknowledge: the receipt of this notification, the reading of this notification or/and the hearing of this notification. The processing unit of the connected watch is configured to implement such detection by being connected to the interfaces 9, 10 for broadcasting a visual and sound piece of information, to the input interface 12, and to the microphone 13.

In response to this notification 6, the method comprises a step of designing 111 a multimedia message 7 relating to the particular event lived by the wearer. More particularly, this step comprises a sub step of creating 112 this message 7 from the connected watch 2 by using the specific interface displayed on the interface 9 for broadcasting a visual piece of information of the connected watch. This message 7 can be for example a voice message recorded by the microphone 13 of the connected watch 2. In this context, this specific interface comprises information for assisting the wearer when he is recording this message. Indeed, this specific interface can include graphical information displayed on the interface 9 to guide the wearer during the recording of this message and/or to allow him to control this recording.

Furthermore, this step 111 includes a sub-step that includes completing 113 this multimedia message 7 from the electronic device 3. For instance, this message 7 can be completed with:
- the recorded information regarding the successive emotional factors;
- graphical representations related to the particular event;
- a textual description of the particular event;
- songs related to the particular event;
- etc. . . .

The method comprises a step of sending 114 the multimedia message to a database of a server configured to archive messages, including the multimedia message, that relate to particular events of the wearer. During this step 114, the processing unit 15 executing the application sends the multimedia message 7 to the control unit 17 of the server 4. Then, this control unit 17 stores this multimedia message 7 in the data relating to the information 19 regarding the wearer in the database 5.

It will be apparent to those skilled in the art that various modifications may be made in the present disclosure, without departing from the spirit or the scope of the disclosure. Thus, it is intended that the present disclosure cover modifications and variations of embodiments of the present disclosure.

The invention claimed is:

1. A method for archiving a particular event in a life of a wearer of a connected watch, the method comprising:
    tracking at least one category of emotional factor of the wearer, wherein the tracking comprises detecting a change in measuring data of the at least one category of emotional factor coming from a bio-information sensor included in the connected watch, by monitoring the measuring data that is received by comparing at least one emotional measurement factor measurement, included in the measuring data, to a reference measurement of a corresponding emotional factor, and generating a detection message based on determining that an emotional factor measurement, included in the measuring data, exceeds the reference measurement of corresponding emotional factor during a predetermined period;
    diffusing, by the connected watch to the wearer, a notification of detection of the particular event to the wearer based on a change in the tracked at least one category of emotional factor of the wearer occurring;
    in response to the notification, designing by the wearer on the connected watch a multimedia message relating to the particular event selected by the wearer; and
    sending the multimedia message to a database of a server configured to archive messages, including the multimedia message, that relate to particular events of the wearer,
    wherein the designing the multimedia message comprises creating, on the connected watch, the multimedia message by using a specific interface displayed on an interface in response to detecting that the wearer received the notification for broadcasting a visual piece of information of the connected watch, and
    wherein the multimedia message is a voice message selectively recorded by the wearer through a microphone of the connected watch and the specific interface displayed for broadcasting a visual piece of information comprises information for assisting the wearer when the multimedia message is recorded by the wearer.

2. The method according to claim 1, further comprising a step of displaying on the interface of the connected watch for broadcasting a visual piece of information of the connected watch, the specific interface for entering the multimedia message relating to the particular event lived by the wearer, after the notification has been diffused.

3. The method according to claim 1, wherein the designing the multimedia message comprises completing, by an electronic device, the multimedia message.

4. The method according to claim 1, wherein the diffusing the notification comprises generating the notification based on a detection message.

5. The method according to claim 1, wherein the specific interface comprises graphical information displayed on the interface to guide the wearer during the recording of the multimedia message.

6. A non-transitory computer-readable medium storing computer instructions configured to cause at least one processor of an electronic device, that is connected to a watch, to implement the method of claim 1.

7. A system for archiving a particular event in a life of a wearer of a connected watch, implementing the method according to claim 4, the system comprising the connected watch and an electronic device configured for tracking at least one category of emotional factor of the wearer wherein the tracking comprises detecting a change in measuring data of the at least one category of emotional factor coming from a bio-information sensor included in the connected watch, by monitoring the measuring data that is received by comparing at least one emotional measurement factor measurement, included in the measuring data, to a reference measurement of a corresponding emotional factor, and generating a detection message based on determining that an emotional factor measurement, included in the measuring data, exceeds the reference measurement of corresponding emotional factor during a predetermined period, in this system the connected watch is also configured for:
    diffusing to the wearer, a notification of detection of the particular event to the wearer based on a change in the tracked at least one category of emotional factor of the wearer occurring;
    in response to the notification, designing by the wearer of the watch a multimedia message relating to the particular event selected by the wearer; and
    sending the multimedia message to a database of a server of this system which is configured to archive messages, including the multimedia message, that relate to particular events of the wearer,
    wherein the designing the multimedia message comprises creating, on the connected watch, the multimedia message by using a specific interface displayed on an interface in response to detecting that the wearer received the notification for broadcasting a visual piece of information of the connected watch, and
    wherein the multimedia message is a voice message selectively recorded by the wearer through a microphone of the connected watch and the specific interface displayed for broadcasting a visual piece of information comprises information for assisting the wearer when the multimedia message is recorded by the wearer.

8. The system according to claim 7, wherein the electronic device is configured for completing the multimedia message during its designing.

9. The system according to claim 7, wherein the connected watch is configured for:
    displaying on the interface of the connected watch for broadcasting a visual piece of information of the connected watch, a specific interface for entering the multimedia message relating to the particular event lived by the wearer directly/immediately after this notification has been diffused, or displaying on the interface for broadcasting a visual piece of information of the connected watch, the specific interface for entering the multimedia message relating to the particular event lived by the wearer solely when the processing unit of the connected watch has detected that the wearer has received this notification, wherein the wearer of the connected watch selects and designs the multimedia message on the connected watch.

10. The method according to claim 5, wherein the specific interface comprises graphical information displayed on the interface to allow the wearer to control the recording of the multimedia message.

* * * * *